(12) United States Patent
Lang

(10) Patent No.: US 6,479,529 B1
(45) Date of Patent: *Nov. 12, 2002

(54) ANTIOXIDANT STABILIZER SYSTEM FOR PHARMACEUTICAL FORMULATIONS

(75) Inventor: Philip C. Lang, Toms River, NJ (US)

(73) Assignee: Shire US Inc., Florence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/290,904

(22) Filed: Apr. 12, 1999

Related U.S. Application Data

(62) Division of application No. 09/057,260, filed on Apr. 8, 1998, now Pat. No. 5,962,488.

(51) Int. Cl.$^7$ .................. A61K 31/42; C07D 261/08
(52) U.S. Cl. .................. 514/378; 514/378; 514/379; 514/380; 548/247
(58) Field of Search ............... 514/378, 379; 548/247

(56) References Cited

U.S. PATENT DOCUMENTS

| | | | |
|---|---|---|---|
| 4,091,091 A | 5/1978 | Terrill | 424/80 |
| 4,837,031 A | 6/1989 | Denton | 434/464 |
| 5,286,753 A | 2/1994 | Schaus et al. | 514/657 |
| 5,389,687 A | 2/1995 | Schaus et al. | 514/657 |
| 5,426,229 A | 6/1995 | Schaus et al. | 564/428 |
| 5,434,174 A | 7/1995 | Gidda et al. | 514/378 |
| 5,639,772 A | 6/1997 | Hammarberg et al. | 514/374 |
| 5,691,352 A | 11/1997 | Ertel et al. | 514/317 |
| 5,962,488 A | * 10/1999 | Lang | 514/378 |

OTHER PUBLICATIONS

The Merck Index, Eleventh Edition, Susan Budavari, Maryadele J. O'Neil, Ann Smith, Patricia E. Heckelman, 1989, pp. 363, 671, 895, 1433.

* cited by examiner

Primary Examiner—Joseph K. McKane
Assistant Examiner—Sonya Wright
(74) Attorney, Agent, or Firm—DeLio & Peterson, LLC

(57) ABSTRACT

Chemically stable pharmaceutical formulations comprising a therapeutically effective amount of a material of formula I are provided which formulations contain a stabilizer system comprising an organic carboxylic acid containing more than 1 carboxylic acid group and an antioxidant. The preferred organic carboxylic acid is citric acid and the preferred antioxidants are ascorbic acid and butylated hydroxytoluene, which antioxidants are preferred to be used in admixture. The chemically stable pharmaceutical formulations are particularly useful for treating Irritable Bowel Syndrome (IBS) in mammals and comprises administering to the mammal needing treatment an effective dose of the above chemically stable pharmaceutical formulation. The stabilizer system is also effective for use in other pharmaceutical formulations containing active ingredients having oxidizable groups such as amino, phenolic, hydryoxyl amino, aldehyde, unsaturated compounds, sulfoxide, sulfone and mercapto. The preferred Formula I compound is as follows:

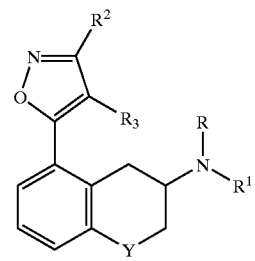

wherein R and $R^1$ are propyl; $R_2$ and $R_3$ are hydrogen; Y is $CH_2$ and the compound is an HCl salt.

8 Claims, No Drawings

ANTIOXIDANT STABILIZER SYSTEM FOR PHARMACEUTICAL FORMULATIONS

This is a divisional of application Ser. No. 09/057,260, filed on Apr. 8, 1998, which issued as U.S. Pat. No. 5,962,488 on Oct. 5, 1999.

BACKGROUND OF THE INVENTION

1. Field of the Invention

This invention relates generally to pharmaceutical formulations and, in particular, to an antioxidant stabilizer system for pharmaceutical formulations containing compounds such as isoxazole derivatives used for the treatment of Irritable Bowel System (IBS).

2. Description of Related Art

Pharmaceutical formulations are made using materials such as antibiotics, antacids, drugs and vitamins and are prepared in a variety of forms including tablets, capsules, ointments, liquids, etc. An overriding problem with any pharmaceutical formulation, however, is the stability of the active ingredient. Stability generally relates to loss of potency but loss of potency may also be accompanied by the formation of by-product materials which are harmful from a health standpoint.

Irritable Bowel Syndrome (IBS) is a motor disorder consisting of altered bowel habits, abdominal pain, and the absence of detectable pathology. IBS is recognized by its symptoms, which are markedly influenced by psychological factors and stressful life situations.

IBS is one of the most commonly encountered gastrointestinal disorders. Between 20% and 50% of patients referred to gastrointestinal clinics suffer from IBS. Symptoms of IBS occur in approximately 14% of otherwise apparently healthy people. It is one of the least understood disorders, in part because it is not a disease but a syndrome composed of a number of conditions with similar manifestations. The major symptoms of IBS (altered bowel habits, abdominal pain and bloating) are manifestations of increased motility in the gut and hyper-secretion of gastric acid.

Current treatment for IBS include pharmaceutical formulations containing compounds that are both direct acting 5-HTIA agonists and M1-cholinergic—receptor selective agents. Since these two characteristics are important to normalize the bowel habits and reduce the abdominal pain and distension of IBS, these agents which have this combination of activities act to normalize gastrointestinal motility and, be useful in the treatment of IBS conditions.

Pharmaceutical formulations and a method for testing IBS in mammals including humans are shown in U.S. Pat. No. 5,434,174, which patent is incorporated herein by reference. The method comprises administering to a mammal in need of IBS treatment, an effective dose of a compound of the formula I.

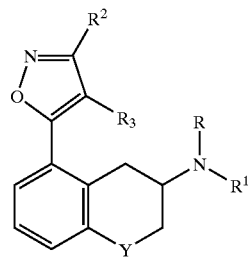

wherein:

R is hydrogen, $C_1$–$C_3$ alkyl, allyl, or

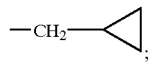

$R^1$ is hydrogen, $C_1$–$C_3$ alkyl, allyl,

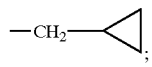

or —$(CH_2)_n$—x;

n is to 1 to 5;

X is an optionally substituted phenyl, $C_1$–$C_3$ alkoxy, or $C_1$–$C_3$ alkylthio;

$R^2$ and $R^3$ are independently hydrogen, $C_1$–$C_3$ alkyl, $C_1$–$C_3$ alkoxy, $C_1$–$C_3$ alkylthio, halo, CN, or phenyl; or together are —$(CH_2)_p$—;

p is 3 to 6;

Y is —$CH_2$—, —O—, —$SO_m$;

m is 0, 1, or 2;

or a pharmaceutically acceptable acid addition salt or solvate thereof.

The '174 patent also discloses pharmaceutical formulations adapted for the treatment of IBS comprising a compound of formula I and a pharmaceutically acceptable carrier, diluent or excipient therefor.

Unfortunately, pharmaceutical formulations made using materials corresponding to compound I and other materials containing oxidizable groups are relatively unstable during storage and lose their potency over time. This, of course, is not acceptable and pharmaceutical formulations having increased storage stability are highly desired.

Bearing in mind the problems and deficiencies of the prior art, it is therefore an object of the present invention to provide a chemically stable pharmaceutical composition comprising therapeutically effective amounts of materials corresponding to a compound of formula I.

It is another object of the present invention to provide a method for treating IBS in humans by administering to the humans in need of treatment an effective dose of a stable pharmaceutical composition containing therapeutical amounts of materials corresponding to a compound of formula I.

Another object of the invention is to provide a stabilizer system for materials corresponding to the compound of formula I.

A further object of the invention is to provide a stabilizer system for pharmaceutical formulations containing materials having oxidizable groups such as amino, phenolic, hydroxyl amino, aldehyde, unsaturated compounds such as alkenes, isoxazole, sulfoxide, sulfone and mercapto and chemically stable pharmaceutical formulations containing the stabilizer system.

Other objects and advantages of the present invention will be readily apparent from the following description.

SUMMARY OF THE INVENTION

The above and other objects and advantages, which will be apparent to one of skill in the art, are achieved in the present invention which is directed, in a first aspect, to a chemically stable pharmaceutical composition comprising:

a therapeutically effective amount of a material corresponding to a compound of formula I;

3

[Chemical structure of formula I showing an isoxazole ring with substituents R2 and R3, connected to a bicyclic chromane-like system with Y and an amine group NRR1]

wherein:
R is hydrogen, $C_1$–$C_3$ alkyl, allyl, or

—$CH_2$—◁ ;

$R^1$ is hydrogen, $C_1$–$C_3$ alkyl, allyl,

—$CH_2$—◁ ;

or —$(CH_2)_n$—X;
n is to 1 to 5;
X is an optionally substituted phenyl, $C_1$–$C_3$ alkoxy, or $C_1$–$C_3$ alkylthio;
$R^2$ and $R^3$ are independently hydrogen, $C_1$–$C_3$ alkyl, $C_1$–$C_3$ alkoxy, $C_1$–$C_3$ alkylthio, halo, CN, or phenyl; or together are —$(CH_2)_p$—;
p is 3 to 6;
Y is —$CH_2$—, —O—, —$SO_m$;
m is 0, 1, or 2;
or a pharmaceutically acceptable acid addition salt or solvate thereof;
an organic carboxylic acid containing more than 1 carboxylic acid group preferably 2 acid groups; and
an antioxidant or mixture of antioxidants.

In another aspect of the invention, a method of treating IBS in mammals including humans comprises administering to the mammal in a need of treatment an effective dose of a chemically stable pharmaceutical composition comprising:
a therapeutically effective amount of a material corresponding to a compound of formula I or a pharmaceutically acceptable acid addition salt or solvate thereof;
an organic carboxylic acid containing more than 1 carboxylic acid group preferably 2 acid groups; and
an antioxidant or mixture of antioxidants.

In a further aspect of the invention, a stabilizer system is provided for pharmaceutical compositions including pharmaceutical compositions comprising a therapeutic amount of a material corresponding to a compound of formula I comprising:
an organic carboxylic acid containing more than 1 carboxylic acid group preferably 2 acid groups; and
an antioxidant or mixture of antioxidants.

In an additional aspect of the invention, a chemically stable pharmaceutical formulation and a method of treating mammals with the chemically stable pharmaceutical formulation are provided wherein the stabilizer system comprises:
an organic carboxylic acid containing more than 1 carboxylic acid group preferably 2 acid groups; and
an antioxidant or mixture of antioxidants.

4

In an additional aspect of the invention, the organic carboxylic acid material containing more than 1 carboxylic group is a dicarboxylic acid and preferably a hydroxy dicarboxylic acid and most preferably an α-hydroxy dicarboxylic acid such as citric acid and tartaric acid. The organic carboxylic acid is admixed with an antioxidant such as the preferred ascorbic acid and a substituted phenol such as butylated hydroxytoluene (BHT). A single antioxidant may be used with the carboxylic acid material but preferably a mixture of antioxidants such as ascorbic acid and derivatives such as ascorbyl palmitate and BHT are used in admixture with the carboxylic acid. The pharmaceutical formulations may contain any of the pharmaceutically accepted carriers, diluents or excipients as is well known in the art.

DESCRIPTION OF THE PREFERRED EMBODIMENT(S)

The general chemical terms used in formula I have their usual meaning. For example, the term "alkyl" represents a straight or branched alkyl chain having the indicated number of carbons. $C_1$–$C_3$ alkyl groups are methyl, ethyl, n-propyl and isopropyl;

—$CH_2$—◁ ;

is cyclopropylmethyl.
Halo refers to bromine, chlorine, fluorine or iodine.
Optionally substituted phenyl means a phenyl ring which may contain one or two substituents from the following list: $C_1$–$C_3$ alkyl, $C_1$–$C_3$ alkoxy, $C_1$–$C_3$ alkylthio, halo, $NO_2$ and CN.

As mentioned hereinabove, useful compounds for practicing the method of the present invention include pharmaceutically acceptable acid addition salts of the compounds defined by the above formula I. Since these compounds are amines, they are basic in nature and accordingly react with any of a number of inorganic and organic acids to form pharmaceutically acceptable acid addition salts. Since the free amines of these compounds are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate and the like as described in U.S. Pat. No. 5,434,174, supra. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates are also included within the scope of this invention.

The compounds of formula I are useful for treating IBS by virtue of their unique ability to modulate function of both the 5-$HT_{1A}$ and muscarinic ($M_1$) receptors in mammals. Preferred classes of formula I are those wherein a) R is $C_1$–$C_3$ alkyl or

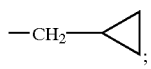;

b) $R^1$ is $C_1$–$C_3$ alkyl or

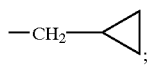;

c) $R^1$ is propyl;
c) $R^2$ and $R^3$ are independently hydrogen or $C_1$–$C_3$ alkyl;
e) $R^2$ and $R^3$ are together —$(CH)_p$—, where p is 3 to 6;
f) Y is O or —$(CH_2)$—.

Especially preferred are those formula I classes wherein
a) R and $R^1$ is propyl;
b) $R^2$ and $R^3$ are independently hydrogen or methyl, preferably hydrogen; and
c) Y is $CH_2$.

Particularly preferred formula I compounds are:
a) 8-(isoxazol-5-yl)-2-di-n-propylamino-1,2,3,4-tetrahydronaphthalene; and
b) 8-(4-methylisoxazol-5-yl)-2-dipropylamino-1,2,3,4-tetrahydronaphtalene;
c) 8-(3-methylisoxazole-5-yl)-2-dipropylamino-1,2,3,4-tetrahydronaphthalene; and
d) acid addition salts thereof.

It will be understood that the above classes may be combined to form additional preferred classes.

The compounds of formula I possess an asymmetric carbon represented by the carbon atom labeled with an asterisk in the following formula:

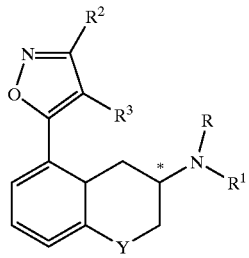

As such, each of the compounds exists as its individual d- and l-stereoisomers and also as the racemic mixture of such isomers. Accordingly, the compounds of the present invention include not only the dl-racemates but also their respective optically active d-and l-isomers.

The compounds of formula I may be prepared by procedures well known to those of ordinary skill in the art and are available by a number of general reactions as shown in U.S. Pat. No. 5,434,174, supra.

The pharmaceutically acceptable acid addition salts of this invention are typically formed by reacting a formula I base with an equimolar or excess amount of acid. The reactants are generally combined in a solvent in which they are soluble such as diethyl ether or benzene, and the salt normally precipitates out of solution within about one hour to 10 days, and can be isolated by filtration.

The term "pharmaceutically effective amount", as used herein, represents an amount of compound of formula I which is capable of binding to both serotonin 1A and $M_1$ receptors. The specific dose of compound formula I administered will, of course, be determined by the particular circumstances surrounding the case, including, for example, the compound administered, the route of administration, and the condition being treated. A typical daily dose is about 0.1 mg to about 10 mg or more of the active compound of formula I. A preferred daily dose is about 0.25 to about 5 mg, and most preferably about 0.5 to about 3 mg.

The compounds of formula I are preferably formulated prior to administration with a pharmaceutically acceptable carrier, diluent or excipient therefore. The pharmaceutical formulations can be prepared by known procedures by using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches such as corn starch, gum acacia, calcium silicate, microcrystalline cellulose, polyvinylpyrrolidone, cellulose, water syrup, methyl cellulose, methylhydroxybenzoates, propylhydroxybenzoates, talc, magnesium stearate, and mineral oil. The formulations may additionally include lubricating agents, wetting agents, emulsifying agents, suspending agents, preserving agents, sweetening agents, flavor agents, and the like. The compositions of the invention may be formulated so as to provide quick, sustained or delayed release of the active ingredient after administration to the patient by employing formulating procedures known in the art.

The compositions including the active ingredient of Formula I are preferably formulated in a unit dosage form, each dosage generally containing up to about 500 mg, and preferably to about 200 mg and most preferably up to about 100 mg. The term "unit dosage form" refers to physically discrete units suitable as unitary dosages for human subjects and other mammals such as a tablet, each unit containing a predetermined quantity of active material calculated to produce the desired therapeutic effect, in association with a suitable pharmaceutical carrier.

The stabilizer system of the invention may also be used with a wide variety of pharmaceutical materials. The invention is particularly directed to the stability of compounds corresponding to formula I wherein oxidation was found to cause the greatest amount of decomposition of the material. The isoxazole ring and the amino, e.g., dipropylamino, moieties are suspected to be the targets of oxidation and the stabilizer system of the invention provides an effective stabilizer system for materials containing these type and other such oxidizable groups. Other pharmaceutical formulations having active ingredients containing similar groups are also contemplated to be protected by the stabilizer system of the invention. In general, pharmaceutical formulations containing active ingredients having the following groups are contemplated herein for use with the stabilizer system of the invention: amino, phenolic, hydroxyl amino, aldehyde, unsaturated compounds such as alkenes, isoxazole, sulfoxide, sulfone and mercapto.

The unit dosage form for such formulations may be up to 1,000 mg or more and are typically up to about 250 mg. The amount of active ingredient is generally about 0.1 to 200 mg and typically about 0.25 to 100 mg.

The stabilizer system of the invention comprises preferably an admixture of an organic carboxylic acid containing more than 1 carboxylic acid group and an antioxidant. An antioxidant may be defined as a material, usually an organic compound, added to a formulation to retard oxidation, deterioration, etc. of the ingredients in the formulation, typically the active ingredient. The organic carboxylic acid is preferably a dicarboxylic acid, and more preferably a hydroxy dicarboxylic acid and most preferably an α-hydroxy dicarboxylic acid selected from citric acid, tartaric acid, fumaric acid, maleic acid and other similar acids, said acids being effective to prevent oxidation/decomposition of materials corresponding to formula I and other materials having oxidizable groups as listed above. The antioxidants are typically substituted phenolic compounds such as butylated hydroxyanisole, propyl gallate and butylated hydroxytoluene (BHT) and ascorbic acid, ascorbyl palmitate, alpha-tocopherol and biflavonoids. Antioxidants such as ascorbic acid and BHT when used in admixture with the organic carboxylic acid provide enhanced stability effects for comounds of Formula I as demonstrated hereinbelow. Because of its demonstrated effectiveness, a preferred stabilizer system comprises citric acid, ascorbic acid and BHT.

The stabilizer system comprising an organic carboxylic acid and an antioxidant will generally contain, by weight, greater than 75% organic carboxylic acid, preferably 80 to 95% and up to about 25% antioxidant, preferably 5 to 20%. It is preferred that an admixture of antioxidants be used in the formulation, but a single antioxidant compound may suitably be employed with the organic carboxylic acid for certain pharmaceutical formulations.

With regard to the use of a stabilizer system in a pharmaceutical formulation, the amount of the stabilizer system can vary widely. Broadly stated, the amount of the stabilizer system in the formulation unit does is, by weight of active ingredient, about 50 to 1,000% or more, preferably 250 to 600%.

Various embodiments of the present invention will now be illustrated by reference to the following specific examples.

It is to be understood, however, that such examples are presented for purposes of illustration only and the present invention is in no way to be deemed as limited thereby. All parts and percentages are by weight in temperatures and degrees centigrade unless otherwise noted.

Typical formulations, for example, are as follows

TABLE 1

| Ingredients | #1 | #2 | #3 |
| --- | --- | --- | --- |
| Formula I Cmpd* | 0.28 | 0.28 | 0.28 |
| Ascorbic Acid USP | 0.10 | 0.30 | 0.10 |
| BHT NF | 0.10 | 0.10 | 0.30 |
| Citric Acid USP | 3.00 | 5.00 | 5.00 |
| Microcrystalline Cellulose NF | 60.0 | 30.0 | 30.0 |
| Corn Starch NF | 35.52 | — | 31.66 |
| Mannitol USP | — | 63.32 | 31.66 |
| Stearic Acid | 1.00 | 1.00 | 1.00 |
| Purified Water | q.s. | q.s. | q.s. |
| Tablet Weight (in mg) | 100.0 | 100.0 | 100.0 |

*R and $R^1$ are propyl; $R^2$ and $R^3$ are hydrogen and Y is $CH_2$ and the compound is in the form of the HCl salt.

The above formulations are made into tables using the following procedure:

1. Pass the microcrystalline cellulose, citric acid, corn starch, and/or mannitol through a mill equipped with a suitable screen. Transfer to a high shear granulator.
2. Dissolve the Formula I Compound in purified water (quantity to be determined).
3. Add the solution of step 2 to the ingredients in the granulator and mix until a uniform, damp granulation is obtained.
4. Transfer the granulation to a Fluid Bed Dryer and allow to dry. Record drying conditions and determine moisture content.
5. Transfer dried granulation to a suitable blender.
6. Pass the ascorbic acid, BHT, and stearic acid through the mill and add to the blender. Blend for 2–3 minutes.
7. Discharge the final granulation into a pre-tared container and record the weight.
8. Compress into tablets of suitable hardness and thickness.

A number of formulations were prepared as shown hereinbelow in Table 1. Formulations were prepared by blending together the ingredients in the amounts (in mgs) indicated below.

TABLE 2

| | FORMULATION | | | | | | |
| --- | --- | --- | --- | --- | --- | --- | --- |
| INGREDIENT | C1 | A1 | A1A | A1B | B1 | B1A | B1B |
| Formula I Cmpd* | 4.562 | 4.562 | 4.562 | 4.562 | 4.562 | 4.562 | 4.562 |
| CITRIC ACID | 20.00 | — | — | — | — | — | — |
| ASCORBIC ACID | 0.781 | — | 0.781 | — | — | 0.781 | — |
| BHT | 0.781 | — | — | 0.781 | — | — | 078.1 |
| MICROCYSTALLINE CELLULOSE | 468.876 | 495.4 | 495.4 | 495.4 | 657.1 | 657.1 | 657.1 |
| CORN STARCH | 500.00 | 500.0 | 500.0 | 500.0 | — | — | — |
| Mg STEARATE | 5.0 | — | — | — | 5.0 | 5.0 | 5.0 |
| DIBASIC CALCIUM PHOSPHATE | — | — | — | — | 333.3 | 333.3 | 333.3 |

*R and $R^1$ are propyl; $R^2$ and $R^3$ are hydrogen and Y is $CH_2$ and the compound is in the form of the HCl salt.

The above formulations were tested for accelerated stability at 40° C. and 80% relative humidity for the time periods indicated below in Table 3.

TABLE 3

| FORM. | TIME PERIOD | IMPURITIES (Relative retention time) | | | | | | | Total New Impurities (approx.) |
|---|---|---|---|---|---|---|---|---|---|
| | | 0.89 | 0.94 | 0.97 | 1.02 | 1.03 | 1.04 | 1.07 | |
| C1 | 2 mo @ 40° C. | 0.1 | — | — | — | — | — | — | 0.1 |
| | 4 mo @ 40° C. | 0.3 | 0.4 | 0.45 | — | — | — | — | 1.2 |
| | 5 mo @ 40° C. | 0.4 | 0.45 | 0.4 | — | — | — | 0.11 | 1.3 |
| A1 | 2 mo @ 40° C. | 1.24 | — | — | — | — | — | 0.2 | 1.4 |
| | 6 mo @ 40° C. | 0.52 | 7.28 | — | 1.95 | 1.72 | 1.87 | 14.85 | 28.0 |
| A1A | 2 mo @ 40° C. | 1.21 | — | — | — | — | — | 0.14 | 1.3 |
| | 6 mo @ 40° C. | 0.4 | 6.02 | — | 2.21 | 1.48 | 1.63 | 12.10 | 24.2 |
| A1B | 2 mo @ 40° C. | 1.5 | — | — | — | — | — | 0.14 | 1.6 |
| | 6 mo @ 40° C. | 0.5 | 6.46 | — | 1.80 | 1.48 | 1.48 | 13.03 | 24.7 |
| B1A | 2 mo @ 40° C. | 0.43 | — | — | — | — | — | 0.12 | 0.7 |
| | 6 mo @ 40° C. | 2.0 | 5.17 | — | — | 1.70 | 2.54 | 0.94 | 14 |
| B1B | 2 mo @ 40° C. | 1.22 | — | — | — | — | — | 0.04 | 1.3 |
| | 6 mo @ 40° C. | 0.6 | 8.99 | 1.62 | 1.19 | 2.78 | 1.26 | 8.00 | 24.3 |

A six month period under these conditions is approximately equivalent to 2 years at 25° C. and 60% relative humidity. The results clearly show the positive effect of citric acid in admixture with the ascorbic acid and BHT antioxidants on the stability of the above formulation.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:
What is claimed is:

1. A chemically stable pharmaceutical composition comprising:
   a therapeutically effective amount of a material containing an active ingredient having at least one group selected from the group consisting of amino, phenolic, hydroxyl amino, aldehyde, unsaturated groups, sulfoxide, sulfone and mercapto;
   an organic carboxylic acid containing 2 or 3 carboxylic acid groups;
   a substituted phenolic compound; and
   ascorbic acid and derivatives of ascorbic acid.

2. The chemically stable pharmaceutical composition of claim 1 wherein the organic carboxylic acid is selected from the group consisting of citric acid, tartaric acid, fumaric acid and maleic acid.

3. The chemically stable pharmaceutical composition of claim 2 containing ascorbic acid and butylated hydroxytoluene.

4. The chemically stable pharmaceutical composition of claim 3 wherein the organic carboxylic acid is citric acid.

5. A stabilizer system for a pharmaceutical composition comprising:
   an organic carboxylic acid containing 2 or 3 carboxylic acid groups;
   a substituted phenolic compound; and
   ascorbic acid and derivatives of ascorbic acid.

6. The stabilizer system of claim 5 wherein the organic carboxylic acid is selected from the group consisting of citric acid, tartaric acid, fumaric acid and maleic acid.

7. The stabilizer system of claim 6 containing ascorbic acid and butylated hydroxytoluene.

8. The stabilizer of claim 7 wherein the organic carboxylic acid is citric acid.

* * * * *

UNITED STATES PATENT AND TRADEMARK OFFICE
CERTIFICATE OF CORRECTION

PATENT NO.     : 6,479,529 B1
DATED          : November 12, 2002
INVENTOR(S)    : Philip C. Lang It is certified that error appears in the above-identified patent and that said Letters Patent is hereby corrected as shown below:

Column 1,
Line 13, delete "System" and substitute therefor -- Syndrome --.
Line 25, delete "bowl" and substitute therefor -- bowel --.

Column 7,
Line 25, delete "comounds" and substitute therefore -- compounds --.

Column 8,
Line 3, after "follows" insert -- : --.
Line 6, Table 2, in column "BIB" delete "078.1" and substitute therefor -- 0.781 --.

Column 9,
Line 5, Table 3, in column "TIME PERIOD" delete "5 mo @ 40°C" and substitute therefore -- 6 mo @ 40°C --.

Column 10,
Line 42, after "stabilizer" insert -- system --.

Signed and Sealed this

Thirteenth Day of May, 2003

JAMES E. ROGAN
*Director of the United States Patent and Trademark Office*